United States Patent
Muller-Dethlefs (10) Patent No.: US 6,868,285 B2
(45) Date of Patent: Mar. 15, 2005

(54) METHOD AND DEVICE FOR DETECTING SUBSTANCES IN BODY FLUIDS BY RAMAN SPECTROSCOPY

(76) Inventor: Klaus Muller-Dethlefs, 14 New Walk Terrace, York, Yorkshire (GB), YO10 4BG ( * ) Notice: Subject to any disclaimer, the term of this patent is extended or adjusted under 35 U.S.C. 154(b) by 0 days.

(21) Appl. No.: 10/296,894

(22) PCT Filed: May 31, 2001

(86) PCT No.: PCT/DE01/02068
§ 371 (c)(1),
(2), (4) Date: May 12, 2003

(87) PCT Pub. No.: WO01/91632
PCT Pub. Date: Dec. 6, 2001

(65) Prior Publication Data
US 2003/0176777 A1 Sep. 18, 2003

(51) Int. Cl.[7] ............................................. A61B 5/00
(52) U.S. Cl. ...................... 600/317; 600/316; 600/365
(58) Field of Search .............................. 600/316–317, 600/365

(56) References Cited
U.S. PATENT DOCUMENTS

| | | | | |
|---|---|---|---|---|
| 5,003,977 A | * | 4/1991 | Suzuki et al. ............... | 600/317 |
| 5,515,847 A | | 5/1996 | Braig et al. ................. | 128/633 |
| 5,553,616 A | | 9/1996 | Ham et al. .................. | 128/633 |
| 5,713,364 A | * | 2/1998 | DeBaryshe et al. ......... | 600/476 |
| 6,044,285 A | * | 3/2000 | Chaiken et al. ............. | 600/316 |
| 6,064,897 A | * | 5/2000 | Lindberg et al. ............ | 600/316 |
| 6,070,093 A | | 5/2000 | Oosta et al. ................. | 600/316 |
| 6,289,230 B1 | * | 9/2001 | Chaiken et al. ............. | 600/322 |
| 6,389,306 B1 | * | 5/2002 | Chaiken et al. ............. | 600/474 |

FOREIGN PATENT DOCUMENTS

| | | |
|---|---|---|
| DE | 19518511 A1 | 11/1995 |
| DE | 69121589 T2 | 1/1997 |
| DE | 19538372 A1 | 4/1997 |
| DE | 69219580 T2 | 9/1997 |
| WO | WO 92/15008 | 9/1992 |
| WO | WO 99/55222 | 11/1999 |
| WO | WO 00/02479 | 1/2000 |

* cited by examiner

Primary Examiner—Eric F. Winakur
Assistant Examiner—Matthew Kremer
(74) Attorney, Agent, or Firm—Perman & Green, LLP (57) ABSTRACT

The invention relates to a method and to a device for the non-invasive detection or determination, by Raman spectroscopy, of the concentration of substances in body fluids. The aim of the invention is to facilitate a non-invasive in vivo detection of substances in body fluids that allows for very accurate, reproducible results of analysis while requiring only little time for measuring which is acceptable for the patient. To this end, the inventive method and device for carrying out a Raman spectroscopy of a body fluid in a body tissue (1) records at least two Raman spectrums under different physical conditions and compares them with each other. The result of comparison allows detection of the substance one is looking for and measurement of the concentration of said substance.

21 Claims, 5 Drawing Sheets

METHOD AND DEVICE FOR DETECTING SUBSTANCES IN BODY FLUIDS BY RAMAN SPECTROSCOPY

This application claims the benefit of the earlier filed International Application No. PCT/DE01/02068, International Filing Date, May 31, 2001, which designated the United States of America, and which international application was published under PCT Article 21 (2) as WO Publication No. WO 01/91632 A1.

BACKGROUND OF THE INVENTION

The invention relates to a method and a device for the non-invasive detection or determination, by Raman spectroscopy, of the concentration of substances in body fluids. In particular the invention is concerned with detection or determination of concentrations of glucose, cholesterol, lactate or such in human blood.

For the detection of substances dissolved in the blood of a patient in most cases a blood sample is taken from the patient and subsequently analysed. Provided this blood sample is taken as outpatient only once or in relatively large intervals and by skilled personnel this is not an excessive inconvenience for the patient. However, if a frequent, recurring investigation of the blood is required in regular intervals as for diabetes patients, a frequent taking of blood samples of the patient in a hospital or in a GP surgery constitutes an excessive inconvenience. For this reason so called "home monitoring" procedures have been developed by which the patient can control himself, independent of when and where. However, this implies that the patient always carries the required instrument with himself. The general disadvantage of these procedures is that the taking of a blood sample in each event carries an infection risk—albeit a very small one. If the required instruments (syringes etc.) are not sterile or not available as sterile a blood investigation is not possible. Even bigger difficulties arise from blood analysis by taking of a blood sample for patients disposed with haemophilia. In each case the blood analysis by taking of a blood sample implies a more or less painful operation and an effort the patient is not always up to.

The blood sample taken in a hospital or a GP's surgery must be analysed in a laboratory by (wet) chemical methods. In the case of the "home monitoring" methods the patient uses dry chemical equipment (minilab), frequently in the form of test strips often integrating the blood sample taking in one instrument together, so the analysis in a specially equipped laboratory is no longer required. The disadvantage of any chemical analysis, however, remains in the very high standards that must be demanded for cleanliness and precision of dosage. In addition, for all in vitro methods, there persists the danger that blood and/or chemicals are released into the environment and with that pathogens can be distributed under circumstances.

The taking of a blood sample, often several times per day, constitutes a big burden for the patient both in terms of his health and psychological condition as well as by the restriction of his mobility.

For this reason methods have been developed that permit an investigation of the blood of a patient in vivo without taking a blood sample and that allow the giving of a result without any significant time delay inevitable for a chemical analysis. In, particular, procedures have been described for the determination of the concentration of medically relevant substances in a patient's body, which are based on the changed physical properties of light by the substances to be detected.

From DE-A-195 18 511 a method is known for the transcutaneous determination of concentrations of substances in human blood without blood sampling. In case of this transcutaneous in vivo determination of concentration of substances in the patient's blood such as glucose, lactate, cholesterol, alcohol, drugs or such, a signal is measured by spectroscopic methods that corresponds to the amount of substance and to the amount of water in a given body region. The substance concentration in water is then determined by obtaining the ratio of the signal value for the substance and for the water from which the value for the concentration in blood of the substance is computed. In particular nuclear spin resonance spectroscopy and, in a more general context next to other spectroscopic methods, also Raman spectroscopy is mentioned.

However, severe problems stand in the way of an application of Raman spectroscopy for concentration measurements of substances in tissue fluids. The intensity of Raman scattering is only small and generally several, orders of magnitude smaller than Rayleigh scattering. For human tissue, due to the inhomogeneous and opaque properties of the medium, the Rayleigh scattering (here combining all scattering processes that do not change the scattered wavelength including the scattering from particles) can even be ca. 10 orders of magnitude stronger than the Raman scattering. This strong Rayleigh scattering "blinds" known detection systems in the region of the wavelength shifted Raman scattering. Other than Rayleigh scattering, depending on the excitation wavelength, human tissue can also show unwanted fluorescence or other perturbing light emission hiding the Raman signals. An additional problem results from the spectral superposition of Raman signals of different other substances with the Raman signal of the substance to be detected. Due to the complex composition of the medium, interfering signals result which can be substantially higher than the measured signals for the substance to be detected.

From DE 691 21 589 T2 a non-invasive method as well as a device is known for measuring the concentration of glucose in the ocular aqueous humour by Raman spectroscopy.

From DE 195 38 372 A1 a method and a device is known for a non-invasive glucose measurement in the eye by Raman spectroscopy.

From DE 692 19 580 T2 the determination is known of the composition and the concentration of an arbitrary gas mixture in the respiratory pathways of a patient by Raman spectroscopy.

SUMMARY OF THE INVENTION

The object of the invention is to provide a method and a device to facilitate a non-invasive detection and analysis of substances in body fluids allowing for a high accuracy and reproducibility while requiring only little time for the measurement which is acceptable for the patient.

According to the invention this object is achieved by the method according to claims 1, 2 and 3, respectively, and by the device according to claims 18, 19 and 20, respectively. The dependent claims are directed to preferred embodiments of the invention.

The underlying principle of the invention is to use the Raman scattering of primary light by a substance to be detected to obtain a signal that is correlated with the concentration of the substance to be detected. In order to exclude or at least minimise perturbations of the measurement of the Raman signal of the substance to be detected, the wavelength spectrum of secondary light is sampled in the region of the Raman spectrum of the substance to be detected for two different primary wavelengths according to the invention. As was found by the inventor the Raman spectrum of the substance to be detected is shifted corresponding to the different primary wavelength, however, the Raman spectrum of the body tissue is more or less identical for both primary light wavelengths. The comparison of the Raman spectra for the first and for the second primary wavelength allows to eliminate the background signal of the body tissue and to gain a signal which is proportional to the concentration of the substance to be detected.

According to first aspect of the invention there is provided a method for the non-invasive determination of a concentration of a substance in a body fluid in a body tissue by Raman spectroscopy comprising the steps: a) irradiating monochromatic primary light of a first wave length $\lambda_1$ into the body tissue, b) recording secondary light that is back scattered by the body tissue and storing the intensity of the secondary light in a first memory according to its wavelength as a first Raman spectral signal for the first primary wavelength, c) irradiating monochromatic primary light of a second wavelength $\lambda_2$ into the body tissue, d) recording secondary light that is back scattered by the body tissue and storing the intensity of the secondary light in a second memory according to its wavelength as a second Raman spectral signal for the second primary wavelength, e) comparing the first Raman spectral signal in the first memory with the second Raman spectral signal in the second memory and generating a compare signal in which spectral structures caused by the body tissue are substantially eliminated, f) determining an intensity of the compare signal at at least one sample wavelength $\lambda_3$ for which the intensity corresponds to the concentration of the substance in the body fluid.

According to a second aspect of the invention there is provided a method for non-invasive determination of a concentration of a substance in a body tissue by Raman spectroscopy comprising the steps: a) irradiating monochromatic primary light of a given wavelength $\lambda$ into the body tissue at a first temperature of the body tissue, b) recording secondary light that is back scattered by the body tissue and storing the intensity of the secondary light in a first memory according to its wavelength as a first Raman spectral signal for the first temperature, c) irradiating monochromatic primary light of a given wavelength $\lambda$ into the body tissue at a second temperature of the body tissue, d) recording secondary light that is back scattered from the body tissue and storing the intensity of the secondary light in a second memory according to its wavelength as a second Raman spectral signal for the second temperature, e) comparing the first Raman spectral signal in the first memory with the second Raman spectral signal in the second memory and generating a compare signal for which spectral structures caused by the body tissue are substantially eliminated, f) determining an intensity of the compare signal at at least one sample wavelength $\lambda_3$ for which the intensity corresponds to the concentration of the substance in the body fluid.

According to a third aspect of the invention there is provided a method for non-invasive determination of a concentration of a substance in a body tissue by Raman spectroscopy comprising the steps: a) irradiating monochromatic primary light of a first wavelength $\lambda_1$ into the body tissue at a first temperature of the body tissue, b) recording secondary light that is back scattered by the body tissue and storing the intensity of the secondary light in a first memory according to its wavelength as a first Raman spectral signal for the first wavelength $\lambda_1$ and for the first temperature, c) irradiating monochromatic primary light of a second wavelength $\lambda_2$ into the body: tissue at a first temperature of the body tissue, d) recording secondary light that is back scattered by the body tissue and storing the intensity of the secondary light in a second memory according to its wavelength as a second Raman spectral signal for the second wavelength $\lambda_2$ and the first temperature, e) comparing the first Raman spectral signal in the first memory with the second Raman spectral signal in the second memory and generating a compare signal for which spectral structures caused by the body tissue are substantially eliminated, f) determining an intensity of the compare signal at at least one sample wavelength $\lambda_3$ g) repeating steps a) to f) for a second temperature and generating a second compare signal at at least one sample wavelength $\lambda_3$ for which the intensity of the secondary light for the first and second wavelength are stored in a third and a fourth memory, respectively, and a second compare signal is generated, h) comparing the first and the second compare signal and, depending on the result of this comparison, generating an identification signal at at least one sample wavelength $\lambda_3$.

Preferred embodiments of the methods are distinguished by one or more of the following features:

the primary light of the first and/or second wavelength is irradiated with a preset irradiation frequency and the first and the second Raman spectral signal are recorded with the irradiation frequency;

the irradiation frequency is in the range of some kHz;

the first and the second temperature of the body tissue is adjusted with a preset temperature variation frequency;

the temperature variation frequency corresponds to the heart rate;

the primary light of the first and/or second wavelength is pulsed with a pulse length in the picosecond region;

the primary light is generated by a laser;

the secondary light is recorded in the Stokes region and/or the anti-Stokes region of the Raman spectrum;

the wavelength $\lambda_1$ and $\lambda_2$ of the primary light lie between 750 nm and 850 nm;

the modulus of the difference of the primary light wavelengths $\lambda_1$ and $\lambda_2$, respectively, and the sample wavelength $\lambda_3$ is less than 250 meV (2000 cm$^{-1}$);

the modulus of the difference of the primary light wavelengths $\lambda_1$ and $\lambda_2$, respectively, and the sample wavelength $\lambda_3$ is greater than 2.5 meV (20 cm$^{-1}$);

at least one notch filter is used for eliminating Rayleigh scattering;

an excitation light wavelength $\lambda_{exc}$ is irradiated into the body tissue essentially at the same time as the primary light that is absorbed by the sought after substance;

the wavelength $\lambda_{exc}$ of the excitation light lies between 1.2 $\mu$m and 3 $\mu$m.

Corresponding to the above methods the following devices are provided according to the invention.

According to, a fourth aspect of the invention there is provided a device for the non-invasive determination of a concentration of a substance in a body fluid in a body tissue by Raman spectroscopy comprising: a) a first light source for irradiating monochromatic primary light of a first wavelength $\lambda_1$ into the body tissue, b) a photo detector means for recording secondary light that is backscattered from the body tissue, c) a first memory for storing the intensity of the secondary light according to its wavelength as a first Raman spectral signal for the first wavelength $\lambda_1$, d) a second light source for irradiating monochromatic primary light of a second wavelength $\lambda_2$ into the body tissue, e) a second memory for storing the intensity of the secondary light according to its wavelength as a second Raman spectral signal for the second wavelength $\lambda_2$, f) a comparator means for comparing the first Raman spectral signal; in the first memory with the second Raman spectral signal in the second memory and for generating a compare signal for which spectral structures caused by the body tissue are substantially eliminated, g) a discriminator unit for determining an intensity of the compare signal at at least one sample wavelength $\lambda_3$ for which the intensity corresponds to the concentration of the substance in the body fluid.

According to a fifth aspect of the invention there is provided a device for the non-invasive determination of a concentration of a substance in a body fluid in a body tissue by Raman spectroscopy comprising: a) a light source for irradiating monochromatic primary light of a given wavelength $\lambda$ into the body tissue, b) a heating means for adjusting a first temperature and a second temperature in the body tissue, c) a photo detector means for recording secondary light that is backscattered from the body tissue, d) a first memory for storing the intensity of the secondary light according to its wavelength as a first Raman spectral signal for the first temperature and a second memory for storing the intensity of the secondary light according to its wavelength as a second Raman spectral signal for the second temperature, e) a comparator means for comparing the first Raman spectral signal in the first memory with the second Raman spectral signal in the second memory and for generating a compare signal for which spectral structures caused by the body tissue are substantially eliminated, f) a discriminator unit for determining an intensity of the compare signal at at least one sample wavelength $\lambda_3$ for which the intensity corresponds to the concentration of the substance in the body fluid.

According to a sixth aspect of the invention there is provided a device for the non-invasive determination of a concentration of a substance in a body fluid in a body tissue by Raman spectroscopy comprising: a) a first light source for irradiating monochromatic primary light of a first wavelength $\lambda_1$ into the body tissue, b) a second light source for irradiating monochromatic primary light of a second wavelength $\lambda_2$ into the body tissue, c) a heating means for adjusting a first temperature and a second temperature in the body tissue, d) a photo detector means for recording secondary light that is backscattered from the body tissue, e) a first memory for storing the intensity of the secondary light according to its wavelength as a first Raman spectral signal for the first wavelength $\lambda_1$ and for the first temperature, a second memory for storing the intensity of the secondary light according to its wavelength as a second Raman spectral signal for the second wavelength $\lambda_2$ and for the first temperature, a third memory for storing the intensity of the secondary light according to its wavelength as a third Raman spectral signal for the first wavelength $\lambda_1$ and for the second temperature and a fourth memory for storing the intensity of the secondary light according to its wavelength as a fourth Raman spectral signal for the second wavelength $\lambda_2$ and for the second temperature, f) a first comparator means for comparing the first Raman spectral signal in the first memory with the second Raman spectral signal in the second memory and for generating a compare signal for which spectral structures caused by the body tissue are substantially eliminated, g) a second comparator means for comparing the third Raman spectral signal in the third memory with the fourth Raman spectral signal in the fourth memory and for generating a compare signal for which spectral structures caused by the body tissue are substantially eliminated, h) a third comparator means for comparing the first compare signal with the second compare signal for generating a third compare signal depending on the result of this comparison, i) a discriminator unit for determining an intensity of the third compare signal at at least one sample wavelength $\lambda_3$, j) an output unit for the output of an identification signal according to the intensity at at least one sample wavelength $\lambda_3$ for which the intensity corresponds to the concentration of the substance in the body fluid.

Preferred embodiments of the means are distinguished by one or more of the following features:

the first and/or second light source, the photo-detector means and the first and third, respectively, and/or second and fourth memory, respectively, is/are pulsed with a preset irradiation frequency;

the irradiation frequency is in the range of a some kHz;

the heating means for adjusting the first and second temperature of the body tissue is triggered with a preset temperature variation frequency;

a receiver means is provided for recording the heart rate and the temperature variation frequency is the heart rate;

the first and/or second light source generates pulses of a pulse length in the picosecond region;

the first and/or second light source is a laser;

the first and/or second light source generates a primary light wavelength $\lambda_1$ and $\lambda_2$, respectively, between 750 nm and 850 nm;

at least one notch filter is positioned between the projection optics and the photo detector assembly to eliminate Rayleigh scattering;

a third light source is provided for generating an excitation light wavelength $\lambda_{exc}$ which is absorbed by the substance;

the third light source generates light of a wavelength $\lambda_{exc}$ between 1.2 $\mu$m and 3 $\mu$m;

the third light source is a laser for generating picosecond pulses.

One of several advantages of the methods according to the invention consists in allowing a continuous instead of a merely discreet monitoring of the values of the blood analysis. Furthermore, permanent injury of the patient's tissue by taking blood samples can be avoided as well as possibly accompanied tissue inflammation and enhanced danger of infection. The more selective methods and embodiments according to the invention, producing signals with a better signal to noise ratio, allow for very good reproducibility and accuracy of the analysis in short measurement intervals.

Additional advantages, features and possible applications of the present invention ensue from the following description of examples of embodiments with reference being made to the accompanying drawings.

BRIEF DESCRIPTION OF THE DRAWINGS

The FIGS. 1, 2 and 3 do not show the optical means to scale.

DETAILED DESCRIPTION OF THE PREFERRED EMBODIMENTS

Figure 1:
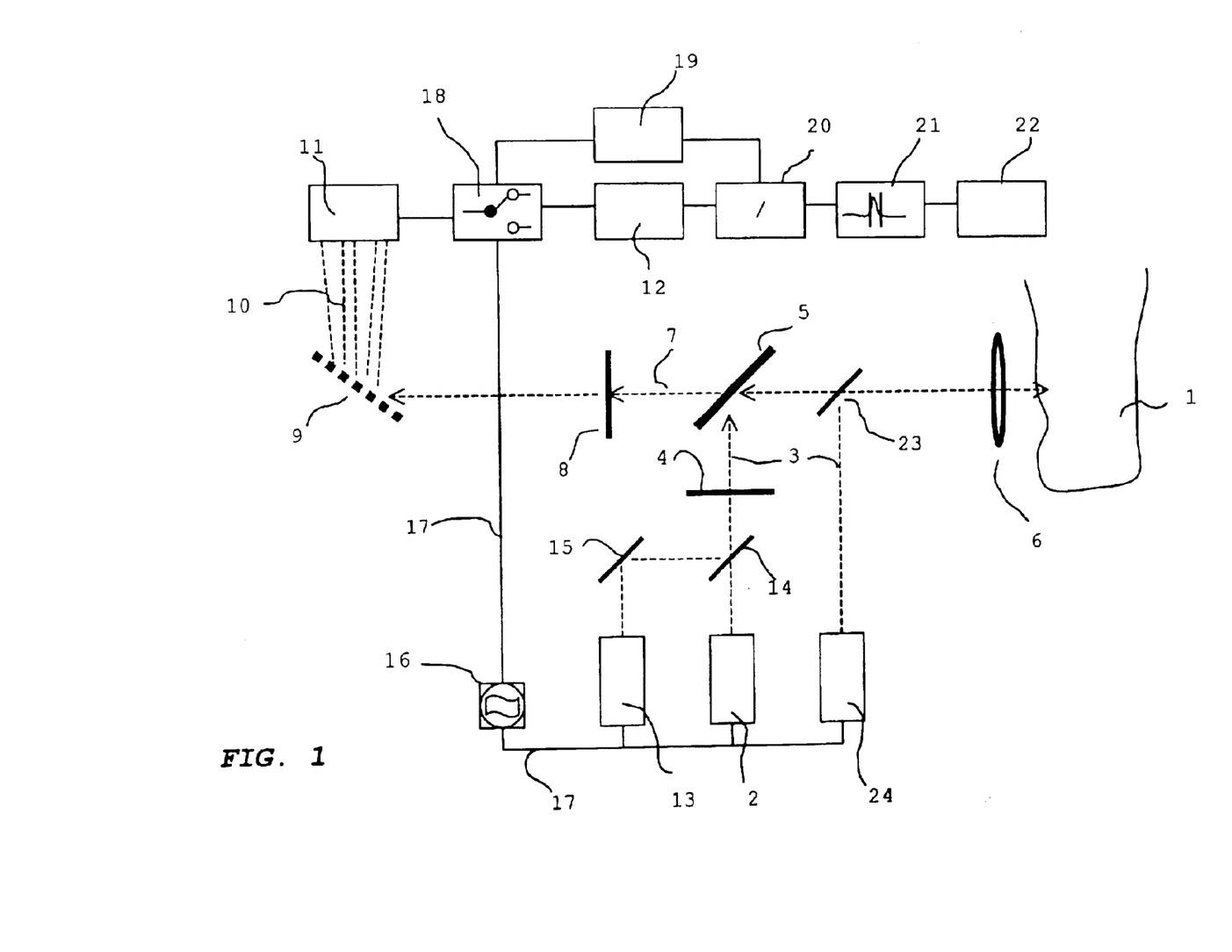
FIG. 1 shows a device for the implementation of the method according to the first aspect of the invention.

FIG. 1 shows an embodiment of the basic set up for the implementation of an embodiment of the method according to the invention. The device for the non-invasive determination of a concentration of a substance in a body tissue 1 by Raman spectroscopy comprises a first light source 2 that serves for irradiating monochromatic primary light 3 of a first wavelength $\lambda_1$ into body tissue 1. Primary light 3 passes through a first optical filter 4 that filters out remaining light, possibly present, of a wavelength other than $\lambda_1$. This band pass filter 4 is particularly of advantage when a non-monochromatic light source 2 is used. The primary light 3 subsequently hits the output beam splitter 5 whose function is explained below. Behind an output beam splitter 5A a projection/collection optics 6 is arranged, projecting primary light 3 onto a spot of body tissue 1. In the shown embodiment the primary light 3 is focussed on an earlobe of a patient which is indicated on the right hand side in FIG. 1.

In the shown embodiment of the device the secondary light that is backscattered from the body tissue 1 is collected by the same projection/collection optics 6. This is particularly advantageous since only one optical component has to be provided thus automatically ensuring that the secondary light originates exactly from the same spot of body tissue 1 which is irradiated by primary light 3. However, it is also possible to arrange the projection optics for the primary light 3 and the collection optics for the secondary light, independently from each other.

Secondary light 7 propagates collinearly to primary light 3 along a short path but in opposite direction and penetrates through the output beam splitter 5. In the output beam splitter 5 the secondary light is branched off the primary light path 3 and it passes through the beam splitter 2 on a path 7 that is different from the primary light path. The separation of primary light 3 and secondary light 7 in beam splitter 5 may depend on the wavelength or the polarisation selectively. This is generally known to a person skilled in the art and needs no further explanation here. The secondary light 7 passes through a second optical filter 8 in which unwanted scattered light is filtered out. This second optical filter 8 is optional as well as the first optical band pass filter 4. The filter 8 mainly serves for the elimination of Rayleigh scattering (scattering without change of wavelength).

Preferably notch filters are used as optics 5 and 8, respectively. Due to the angular dependence of the reflectivity of notch filters the intensity of the transmitted light can be adjusted by the choice of the respective angle of incidence. With that the angle of incidence of beam splitter 5 is preferably adjusted to 10 degrees.

In a dispersing element 9 (grating, prism) the secondary light 7 is split into spectrally dispersed secondary light 10 that itself is collected by a photo-detector means 11. The photo-detector means 11 is preferably a multi-channel detector such as a CCD camera or a photodiode array.

The signal from the photo-detector means 11 is stored in a first memory 12 as intensity signal of the secondary light 7 as a function of wavelength, namely as first Raman spectral signal in memory 12. This stored spectrum is the spectrum for a first primary wavelength $\lambda_1$. In the process of selecting which channels of the multi-channel detector means 11 are read, a restriction to a preset wavelength region can be carried out additionally to the optical and electronic restrictions.

A second light source 13 is provided for the generation of monochromatic primary, light 3 of a second wavelength $\lambda_2$. The primary light from this second light source 13 is coupled into the beam path of the first light source 2 via a first beam splitter 14 and a second beam splitter 15 so that the primary light 3 of a second wavelength $\lambda_2$ is irradiated into the body tissue 1 on a path identical to, the primary light 3 of first wavelength $\lambda_1$.

The intensity of secondary light 7 is stored according to its wavelength as a second Raman spectral signal in a second memory 19 analogously to the above, for which an additional electronic restriction on a pre-set wavelength region can also take place optionally. This stored spectrum is the spectrum for the second primary light wavelength $\lambda_2$.

The switching over of the output of the photo-detector means 11 to the second memory 19 ensues by a switching gate 18 which is connected between the photo detector means 11 on one hand and the first memory 11 and second memory 19, respectively, on the other hand. The switching gate 18 is triggered by a system clock 16 via electrical control lines 17 synchronously to the first light source 2 and the second light source 13 so that memory 12 and 19 store only their "own spectrum" and no overlap comes about of spectra in memory 12 and 19.

In a comparator means 20 a comparison is made between the first Raman spectral signal in the first memory 12 and the second Raman spectral signal in the second memory 19 and a compare signal is generated for which spectral structures caused by body tissue 1 are substantially eliminated and only features of the secondary light remain which are caused by the substance to be detected in the body tissue and in the body fluid, respectively. In particular the comparator unit 20 can be a subtraction unit that subtracts the two Raman spectra in memory 12 and 19, respectively, from each other. However, a divider can be employed as comparator unit 20 as well and further mathematical procedures for processing the data before and after the comparison can be used as well.

As mathematical procedures for processing the data before and after the comparison well known multivariate statistical methods can be used, among others partial linear regression, principle component analysis (PCA) and principle component regression (PCR). In the course of this a number of measured Raman spectral signals obtained at variable glucose concentrations is analysed by a multivariate statistical method. In contrast to the simple calculation of the difference of two signals these statistical methods allow for a particularly good recognition of the glucose spectrum (pattern recognition) with respect to the background and with that allow for a more exact determination of the glucose concentration. For the practical application on a patient a number of Raman spectra, as high as possible, is recorded at different times and stored. Each of the Raman spectra stored corresponds, as variable, to a certain glucose concentration in blood. The more Raman spectra become available for the multivariate statistical analysis as a function of glucose concentration the better and more accurately the glucose concentration can be determined from the statistical regression analysis.

In detail, for the method for the non-invasive determination of a concentration of a substance in a body-fluid in a body tissue 1 by Raman spectroscopy, monochromatic primary light 3 of a first wavelength $\lambda_1$ is irradiated into the body tissue 1 at a first parameter value. Consecutively, secondary light 7 that is back scattered by the body tissue and is collected and the intensity of the secondary light as a function of its wavelength is stored as a first Raman spectral signal for the first primary wavelength ($\lambda_1$) in a first memory 12. Both these steps of irradiating the primary wavelength and collecting and storing the secondary light are repeated at other primary wavelengths and further parameter values as well. The intensity of the secondary light 7 is stored in a further memory for each further primary wavelength $\lambda_1$, $\lambda_j$, $\lambda_k$ etc. and for each further parameter value. Finally, the Raman spectral signals are compared using a multivariate statistical method for the determination of at least one sample wavelength $\lambda_3$ for which the intensity behaves analogously to the changes of the parameter values that is the intensity changes according to the parameter values. The intensity at at least one sample wavelength $\lambda_3$ is determined in several Raman spectral signals and it is output as a function of the parameter values.

Preferably this parameter constitutes the blood sugar level of the patient, that is several spectra are measured over a longer time scale for which the blood sugar level changes (for instance 20 spectra over one day) and compares these using multivariate statistical methods.

The features in the compare signal, which go back to the substance to be detected in the body fluid and in the body tissue, respectively, are analysed in a discriminator unit 21. In particular, the intensity is determined of the compare signal at at least one sample wavelength $\lambda_3$, at which a signal of the sought after substance is expected, in which the intensity corresponds to the concentration of the substance in the body fluid.

The result of the measurement is output through an output means 22, where this output means 22 may be a simple screen, a printer or a PC with all corresponding and well known output options.

Figure 4A:
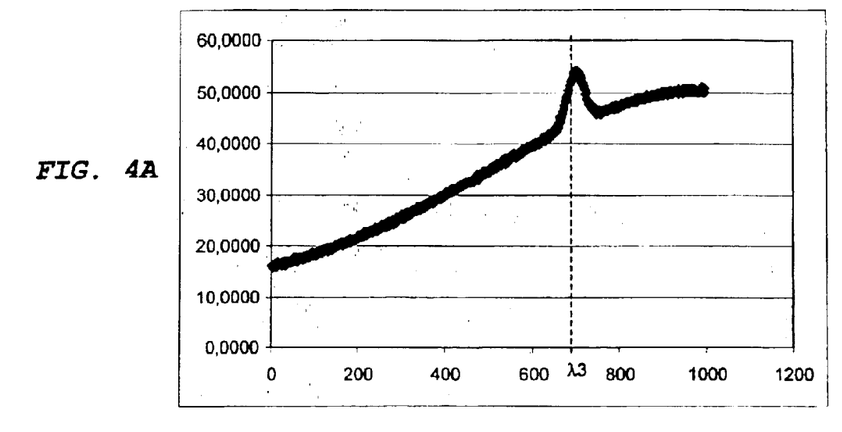
FIGS. 4A, B and C show a first spectral signal for a first primary light wavelength, a second spectral signal for a second primary light wavelength and, respectively, the difference spectrum of both spectral signals from FIGS. 4A and 4B according to the invention.
Figure 4B:
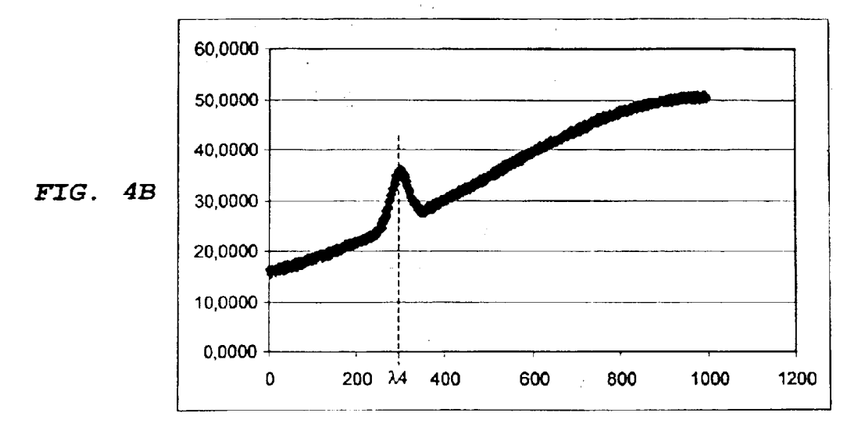
Figure 4C:
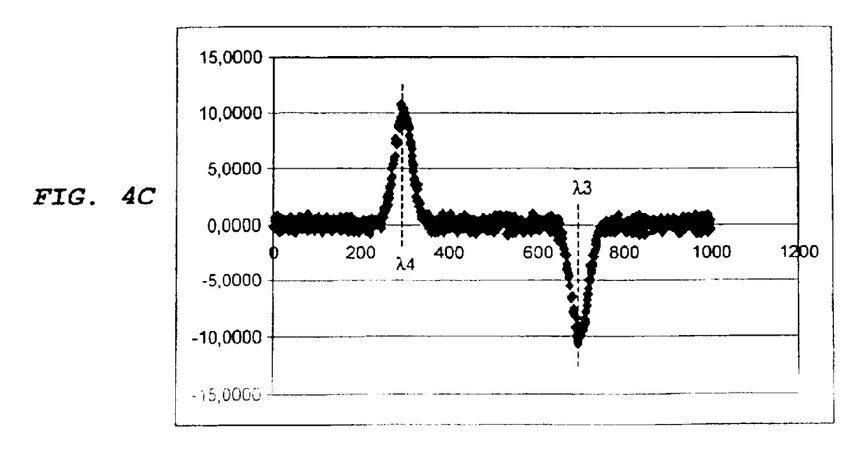

A simulation is shown in FIGS. 4A to C of the Raman spectra in the first memory 12, the second memory 19 and in the discriminator unit 21. In FIGS. 4A to 4C the wavelength of the spectrally dispersed secondary light 10 is plotted on the abscissa as channel number of photo detector means 11. The strength of the signal received by the photo detector means 11 corresponds to the light intensity, and it is plotted on the ordinate in arbitrary units. Essentially, the spectrum in FIG. 4A shows an intensity distribution that increases towards higher channel numbers (wavelength) that is towards the right part of the spectrum. There is a Raman line at a wavelength $\lambda_3$ superimposed on this intensity distribution (shown here is only one e.g. the Stokes line, but in fact there are two lines to be expected, namely in addition to the Stokes also an anti-Stokes line, which is weaker, though).

Essentially the same spectrum is generated at second wavelength of the primary light, shown in FIG. 4B, in which the background (sloped towards the right) is essentially unstructured and unchanged compared to the spectrum in FIG. 4A, which was taken at the first primary light wavelength. Again in FIG. 4B a Raman line, now at wavelength $\lambda_4$, is superimposed on the broad baseline slope. The energy difference between the Raman line at a wavelength $\lambda_3$ in the first spectrum and at a wavelength $\lambda_4$ in the second spectrum corresponds to the energy difference between the first and the second primary light wavelength $\lambda_1$ and $\lambda_2$ of the first second light source 13, respectively.

In FIG. 4C the difference spectrum is shown of both spectra in FIGS. 4A and 4B, with the background being eliminated that is due to the surrounding body tissue. With that the intensity can be determined unambiguously of both Raman lines at wavelength $\lambda_3$ and $\lambda_4$, respectively, (except for the sign) and this intensity is a measure for the concentration of the sought after substance. (In addition in the difference spectra there appear also corresponding anti-Stokes lines, not shown here, which optionally can be taken into account for the determination of the concentration).

Furthermore, in the embodiment according to FIG. 1, a third light source 24 is provided whose light is coupled, by a beam splitter 23, into the beam path between the first light source 2 and the projection/collection optics 6. (The beam path in this and in the following figures is only to be understood symbolically. For a person skilled in the art it is clear that the precise construction of the optics depends on the relative transmission and reflection properties of the optical elements used. Correspondingly the beam splitter 23 can also be placed between photodetector 9 and beam splitter 5. Optionally the light from the third light source 24 can be irradiated into the body tissue 1 independently of the first light source 2 and the second light source 13.) A notch filter can also be employed for beam splitter 23 which reflects light of the wavelength of the third light source and transmits all other wavelengths, in analogy to beam splitter 5. The third light source 24 is activated shortly before the first and second light source 2 and 13, respectively. This allows preparing the sought after molecule, for instance, higher vibrational states of the molecule can be populated, respectively lower, vibrational states of the molecule, can be de-populated. With this, intensity differences can be induced in the spectral signal and the selectivity for Raman excitation of the sought after substance by the primary light is enhanced. In particular this procedure can be employed for anti-Stokes transitions, which under circumstances are only facilitated this way. With that a particularly sensitive measurement probe is established. Hence the wavelength $\lambda_{exc}$ generated by the third light source 24 lies between 1.2 $\mu$m and 3 $\mu$m. In this spectral region the body tissue is essentially transparent. Also in this region a laser is preferably used as light source 24.

For reasons of relaxation of the excited state generated by the third light source 24 in the sought after molecule, the first, second and third light sources 2, 13 and 24 preferably produce pulses with a pulse length in the picosecond range. This can be particularly well achieved with lasers as light source.

Figure 2:
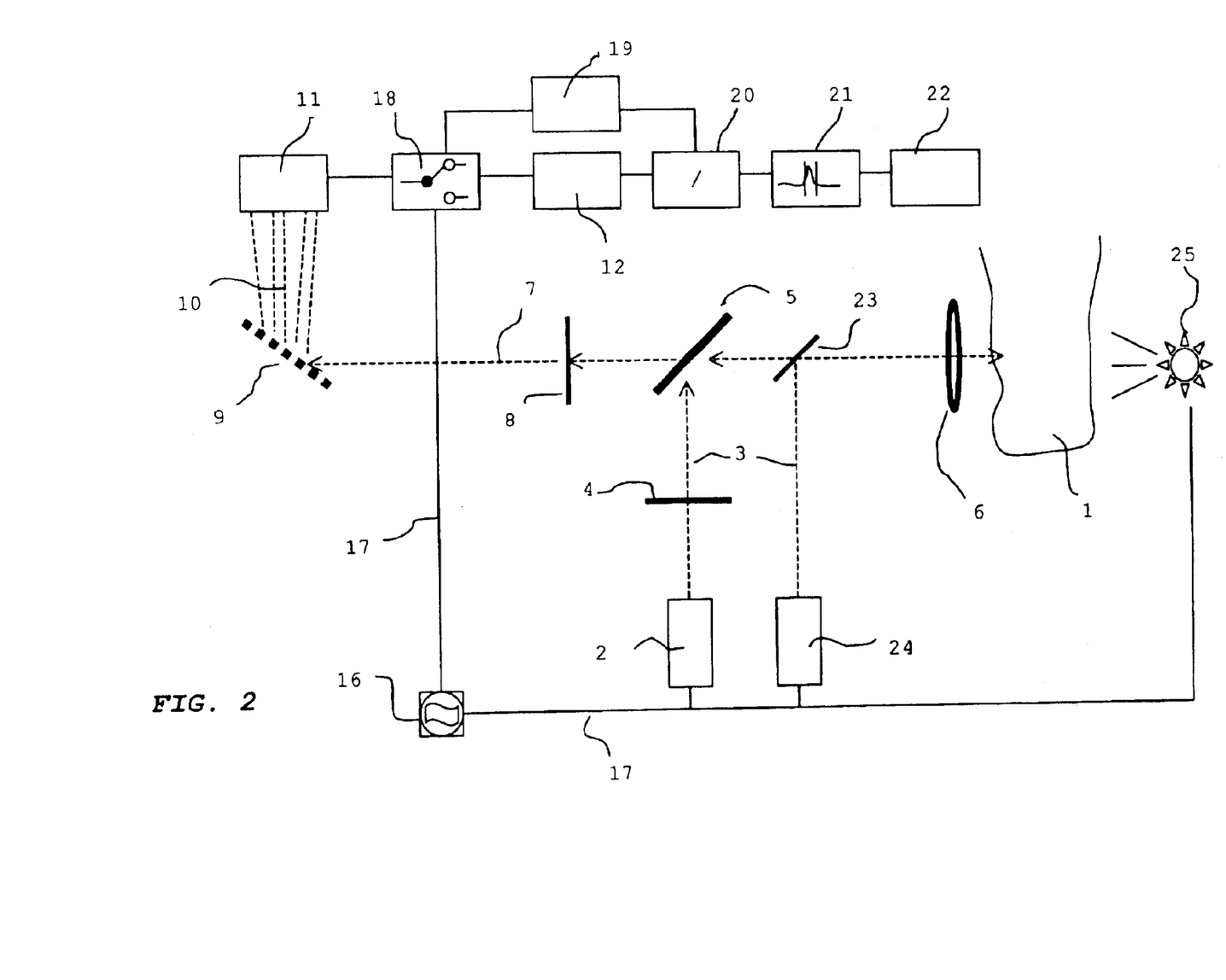
FIG. 2 shows a device for the implementation of the method according to the second aspect of the invention.

In FIG. 2 an alternative device is shown for the non-invasive determination of a concentration of a substance in a body fluid in a body tissue 1 by Raman spectroscopy, for which the same components, as those for the device according to FIG. 1, are denoted by the same reference numerals and are not explained once more. This second means is based on the detection of the temperature dependence of the measurement signal. The construction of this device is essentially identical to that of the device according to FIG. 1, merely the second light source is missing in FIG. 2. Therefore a light source 2 is employed for irradiating monochromatic primary light 3 of a preset wavelength $\lambda$ into body tissue 1. Instead of a second light source a heating means 25 is employed for adjusting a first temperature and a second temperature in body tissue 1, for which heating means 25 is preferably an infra-red radiator depicted by a star structure on the right hand side in FIG. 2.

Identical to the corresponding elements in FIG. 1 are the optical elements 4 to 6 and 8 as well as the photodetector means 11, with dispersing element 9 for the detection of secondary light 7 backscattered from body tissue 1, the first memory 12 for storing the first Raman spectral signal and the second memory 19 for storing the second Raman signal, as well as a comparator means 20 and a discriminator means 21.

The measurement is first carried out at a first temperature $T_1$ of body tissue 1 and the corresponding spectrum is stored in the first memory 12. After that the measurement is repeated with the same primary wavelength $\lambda$ at a second temperature $T_2$ and the second spectrum is stored in the second memory 19. The comparison and evaluation of the spectra is carried out in the same way as above for the means according to FIG. 1.

Figure 5A:
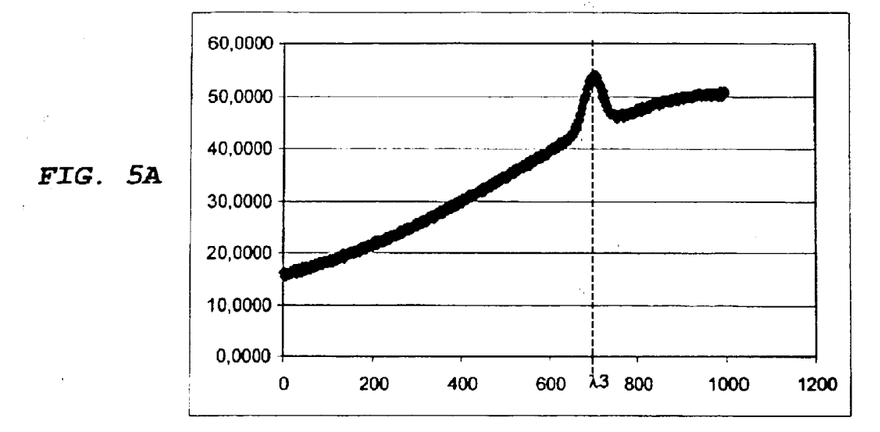
FIGS. 5A, B and C show a first spectral signal for a first temperature, a second spectral signal for a second temperature and, respectively, the difference spectrum of both spectral signals from FIGS. 5A and 5B according to the invention.
Figure 5B:
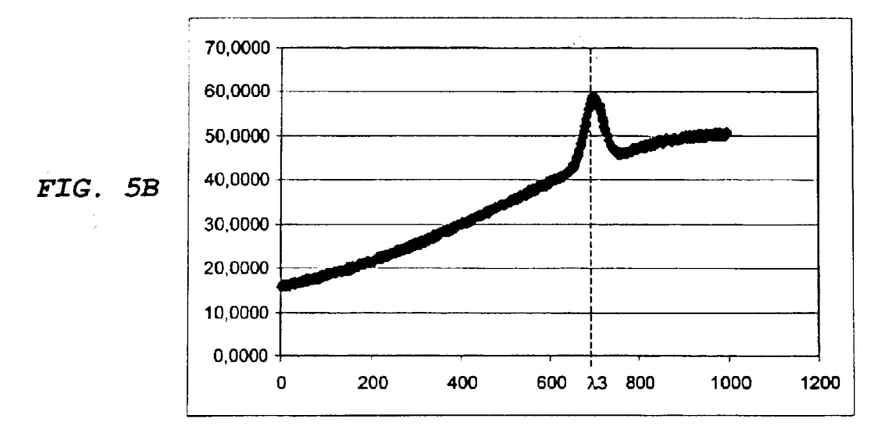
Figure 5C:
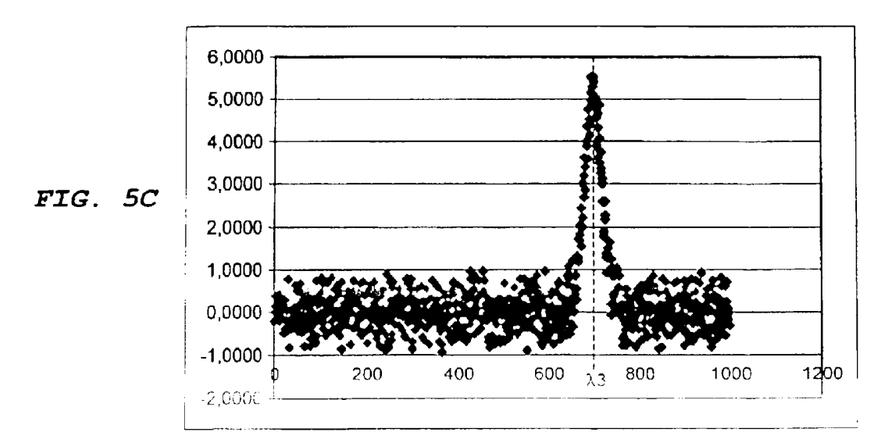

FIGS. 5A to C represent the corresponding spectra in the first memory 12, the second memory 19 and the discriminator unit 21. Here, both Raman lines are at the same wavelength $\lambda_3$ since the excitation wavelength $\lambda$ has not been changed, hence the scattered line has the same length in both measurement stages. In the remaining part the spectra in FIGS. 5A and 5B show a broadly sloped background which according to the inventor's observations can be traced back to the body tissue and hence is not caused by the sought after substance.

The difference spectrum in FIG. 5C contains only one line in contrast to the spectrum in FIG. 4C, namely the one at wavelength $\lambda_3$. Also at this line the intensity is a measure for the concentration of the substance in the body fluid.

Figure 3:
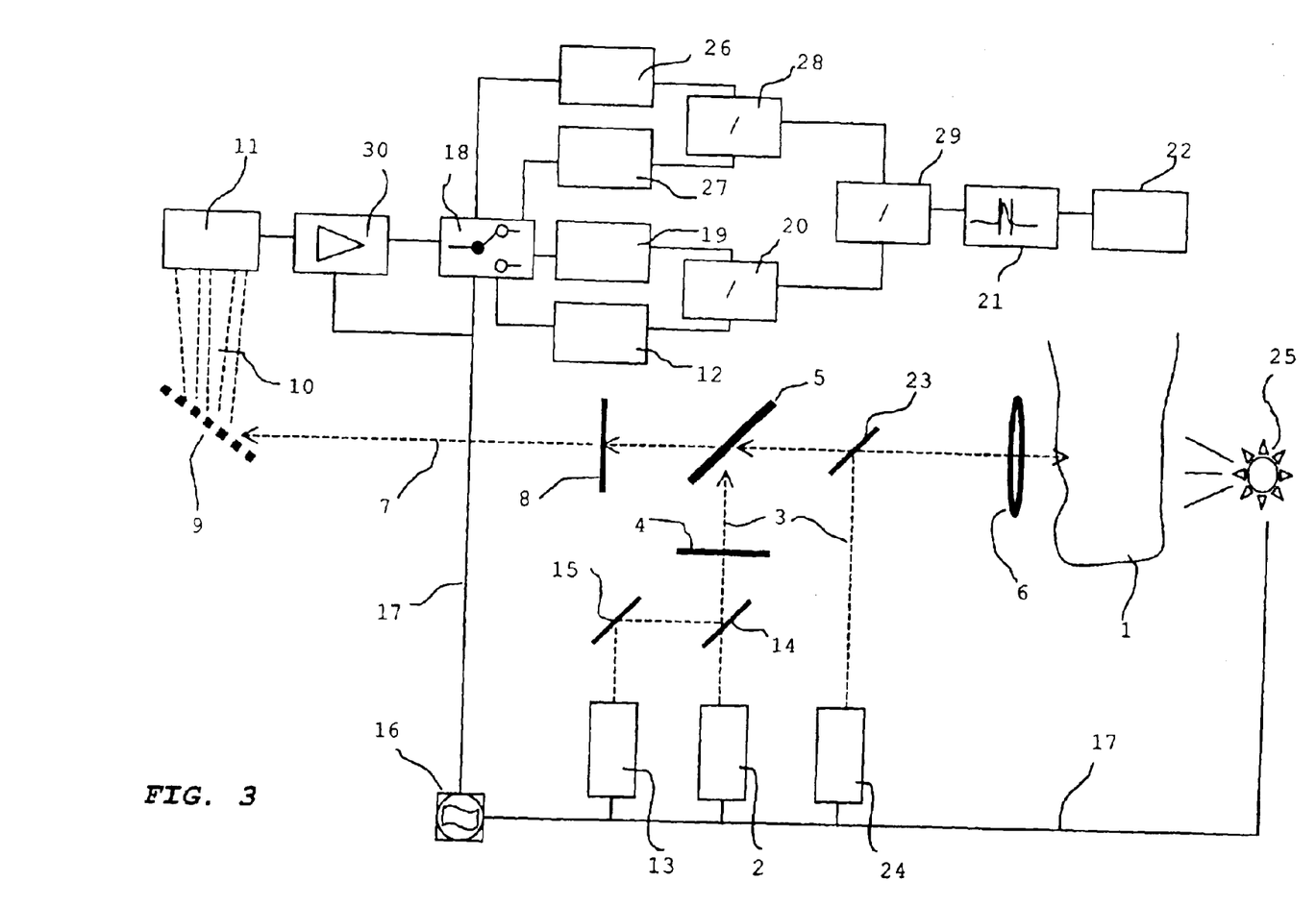
FIG. 3 shows a device for the implementation of the method according to the third aspect of the invention.

For some substances the Raman signal is very weak. For a successful filtering out the Raman signal of the sought after substance from the background signal of the body tissue, which may be extremely difficult, several different parameters have to be changed simultaneously in order to obtain a sufficient signal. It may even be possible that an intensity measurement is no longer feasible but only a qualitative detection of the substance can be carried out. In FIG. 3 a device is shown for the non-invasive determination of a concentration and, respectively, for the detection of a substance in a body fluid in a body tissue 1 by Raman spectroscopy, in which similar components as for the means according to FIG. 1 or FIG. 2 are denoted by the same reference numerals and are not explained again.

The device according to FIG. 3 includes a first light source 2 and a second light, source 13 for irradiating monochromatic primary light 3 of the first wavelength $\lambda_1$ and second wavelength $\lambda_2$, respectively, into a body tissue 1. Furthermore the device contains a heating means 25 for adjusting body tissue 1 to a first temperature and a second temperature. The spectrally dispersed secondary, light 7 is collected by a photo detector means 11 and a first Raman spectral signal is recorded in a first memory 12 for the first primary wavelength $\lambda_1$ and for the first temperature $T_1$, a second Raman spectral signal is recorded in a second memory 19 for the second primary light wavelength $\lambda_2$ and for the first temperature $T_1$, a third Raman spectral signal is recorded in a third memory 26 for the first primary light wavelength $\lambda_1$ and for a second temperature $T_2$, and a fourth Raman spectral signal is recorded in a fourth memory 27 for the second primary light wavelength $\lambda_2$ and for the second temperature $T_2$.

In a first comparator means 20 a comparison is made between the first Raman spectral signal in the first memory 12 and the second Raman spectral signal in the second memory 19 and a first compare signal is generated, in which spectral structures caused by the body tissue are substantially eliminated.

Analogously, in a second comparator means 28 a comparison is made between the third Raman spectral signal in the third memory 26 and the fourth Raman spectral signal in the fourth memory 27 and a second compare signal is generated, in which spectral structures caused by the body tissue are substantially eliminated.

In a third comparator means 29 the first compare signal from the first comparator means 20 and the second compare signal from the second comparator means 28 are compared with each other and a third compare signal is generated that corresponds to the result of this comparison.

The intensity of the third compare signal at at least one sample wavelength $\lambda_3$ is determined in a discriminator means 21 and an identification signal is issued through an output unit 22. This identification signal indicates if a temperature dependent signal change takes place at at least one sample wavelength $\lambda_3$. Provided the temperature dependent difference is big enough between the first and the second compare signal, an indication can again be derived from that about the concentration of the sought after substance in the body fluid, for the computation of which one goes back onto the known temperature difference between the measurements. With that a very sensitive multiple differential means is created for the detection of substances according to the invention.

Since the measurement can be impaired under circumstances by statistical noise when using the device according to FIG. 3 the first light source 2 and the second light source 13 are utilised in a pulsed mode. Synchronously to the triggering of light sources 2 and 13 by the system clock 16 the photo detector means 11 is operated at a preset irradiation frequency as well as the first memory 12, the second memory 19, the third memory 26 and the fourth memory 27. In this way, for example, hundred measurements are conducted at the first primary wavelength $\lambda_1$ and the first temperature $T_1$, hundred measurements are conducted at the first primary wavelength $\lambda_1$ and the second temperature $T_2$, etc. A lock-in amplifier 30, likewise triggered and synchronised by the system clock 16, is envisaged as intermediate memory for this type of measurement.

Measurement sequences are carried out with a irradiation frequency that lies preferably in the region of some Hz to some kHz so that the recording of hundred measurements for two primary wavelengths is completed within a few minutes at a measurement sequence rate of some Hz to kHz.

The adjustment of the temperature in the body tissue naturally takes somewhat longer so that the frequency is preferably the heart rate with which the heating means 25 is triggered for the setting of the first and second temperature of the body tissue. For that a monitoring device (not shown) for recording the heart rate is provided for the device according to FIGS. 2 or 3.

The light sources produce primary light 3 of wavelength $\lambda_1$ and $\lambda_2$, respectively, between 750 nm and 850 nm for the detection of glucose in body fluids in a body tissue 1. In this wavelength region body tissue 1 is essentially transparent.

With above devices methods can be carried out for the detection, respectively for the determination of concentrations of substances as will be described in the following.

A method for the non-invasive determination of a concentration of a substance in a body fluid in a body tissue 1 by Raman spectroscopy according to the invention comprises as a first step irradiating monochromatic primary light 3 of a first wavelength $\lambda_1$ into the body tissue 1. Secondary light that is back scattered by the body tissue is collected and its intensity is stored according to its wavelength as a first Raman spectral signal in a first memory 12.

A Raman spectrum already contains information about the sought after substance as explained above and depicted in FIGS. 4A, 4B, 5A and 5B. However, because of the highly complex composition of human tissue and blood it is necessary to eliminate the background signal of the body tissue. The procedure according to the invention is based on the detection of a first intensity signal at a wavelength spectrum corresponding to the substance to be detected at the first primary light wavelength ($\lambda_1$) and the following detection of a second intensity signal at a wavelength spectrum corresponding to the second primary light wavelength ($\lambda_2$) that is shifted with respect to the first primary light wavelength. For simplicity glucose is assumed to be the sought after substance in the following; the procedures and devices according to the invention may be applied to different substances correspondingly. Compared to other compounds present in blood and body tissue glucose is a relatively small molecule which in blood or in body tissue shows a sharp Raman spectrum with a line width of ca. 2.5 meV (20 cm$^{-1}$). At a primary light wavelength of ca. 800 nm this corresponds to a line width of ca. 1.3 nm, which is a typical line width of diode lasers in this wavelength region. In contrast, the background Raman spectrum of blood or body tissue, which predominantly originates from very large molecules and from water, is spectrally very broad. Therefore shifting the primary light wavelength by a small multiple of the bandwidth of a Raman transition of glucose, i.e. by a few nm, leads to a clearly pronounced shift for the Raman spectrum of glucose whereas the background Raman spectrum stays more or less unchanged. In accordance with the procedure according to the invention two Raman spectra are recorded for different primary wavelengths. The background spectrum is eliminated by subtracting both Raman spectra and one obtains the Raman spectrum originating from glucose in this different spectrum as spectrum of positive and negative peaks on a baseline. This baseline should be constant in the ideal case. Because of the small but not completely negligible dependence of the background Raman spectrum on the primary wavelength this baseline is not completely constant under real measurement conditions but it shows a very broad structure that can be easily distinguished from the sought after narrow band structures in the spectrum. On this baseline, in accordance with the invention, each vibrational transition of the glucose results in a positive and negative peak with respect to the baseline for which the peak maxima are shifted with respect to each other corresponding to the wavelength difference (wave number difference, energy difference) of the primary light and the intensity signal in the middle between the positive and the negative peak corresponds to that of the baseline. For a known wavelength difference of both primary wavelengths and known band width and peak form of the peaks of the glucose Raman spectrum, an intensity signal can be obtained by data analysis of the difference spectrum and comparison with measured and modelled spectra which is proportional to the glucose concentration.

Therefore the procedure comprises as a further step an irradiation of monochromatic primary light 3 of a second wavelength $\lambda_2$ into the body tissue 1 as well as the collection of secondary light 7 that is scattered back from the body tissue 1, at the second primary wavelength. The intensity of the secondary light is stored according to its wavelength as a second Raman spectral signal for the second wavelength $\lambda_2$ in a second memory 19. The first Raman spectral signal in the first memory 12 and the second Raman spectral signal in the second memory 19 are compared with each other and a compare signal is generated for which spectral structures that are caused by the body tissue are substantially eliminated. The concentration of the substance in the body fluid is determined from the intensity of the compare signal at at least one sample wavelength $\lambda_3$.

Analogously, for the device according to FIG. 2, a procedure is carried out for the non-invasive determination of a concentration of a substance in a body fluid in a tissue by Raman spectroscopy comprising the steps: a) irradiating monochromatic primary light 3 of a given wavelength $\lambda$ into body tissue 1 at a first temperature of the body tissue, b) recording secondary light 7 that is back scattered by the body tissue and storing the intensity of the secondary light in a first memory 12 according to its wavelength as a first Raman spectral signal for the first temperature, c) irradiating monochromatic primary light 3 of a given wavelength $\lambda$ into the body tissue at a second temperature of the body tissue, d) recording secondary light 7 that is back scattered from the body tissue and storing the intensity of the secondary light in a second memory 19 according to its wavelength as a second Raman spectral signal for the second temperature, e) comparing the first Raman spectral signal in the first memory 12 with the second Raman spectral signal in the second memory 19 and generating a compare signal for which spectral structures caused by the body tissue are substantially eliminated, f determining an intensity of the compare signal at at least one sample wavelength $\lambda_3$ for which the intensity corresponds to the concentration of the substance in the body fluid.

The intensity of the Raman scattering is proportional to the occupation of the energy levels from which the scattering occurs; the occupation of energy levels as a function of absolute temperature (in Kelvin) is given by the Boltzmann distribution. In case of an increase of temperature the occupation of molecules in excited vibrational levels is increased and correspondingly the occupation in the lowest vibrational level is lowered (and vice-versa). The intensity signal of the Stokes Raman scattering (on the longer wavelength sides with respect to the primary light wavelength) is hence lowered in case of a temperature increase of the body tissue whereas the intensity signal of the anti-Stokes Raman scattering (on the shorter wavelength side with respect to the primary light wavelength) is increased. A temperature change by 3K causes a change of the Raman signal of the substance to be detected of about 1%. By employing a realistically possible temperature change of ca. 10K for human tissue (e.g. in the forehead) an intensity change of the Raman signal of more than 3% can be achieved. With that the glucose concentration in blood can be determined with the required sensitivity and accuracy.

For the method according to the invention the temperature dependence of Raman scattering is exploited to obtain a signal correlated with the concentration of the substance to be detected. For the determination of the concentration of the substance to be detected in the body tissue, primary light in at least one wavelength region is irradiated into the body tissue and the secondary light is collected and spectrally dispersed. Eliminating of the background signal from blood and body tissue is achieved, according to the invention, by taking the Raman spectrum of the sought after substance at at least two different temperatures of the body tissue. The intensity signal of the Raman spectrum of the substance to be detected depends on the temperature and is different corresponding to the different temperature of the body tissue. In contrast the Raman spectrum of the body tissue itself is more or less independent of its temperature. By subtracting both Raman spectra as well as by data analysis of the difference spectrum and comparison with measured and modelled spectra the background signal of the body tissue can be eliminated and a signal can be gained which is proportional to the concentration of the substance to be detected.

For the qualitative detection of a sought after substance, and for the improvement of sensitivity and accuracy, the method according to the invention for non-invasive determination of a concentration of a substance in a body tissue 1 by Raman spectroscopy according to FIG. 3 comprises the steps: a) irradiating monochromatic primary light of a first wavelength $\lambda_1$ into body tissue 1 at a first temperature $T_1$ of the body tissue, b) recording secondary light 7 that is back scattered by the body tissue and storing the intensity of the secondary light in a first memory 12 according to its wavelength as a first Raman spectral signal for the first wavelength $\lambda_1$ for the first temperature $T_1$, c) irradiating monochromatic primary light 3 of a second wavelength $\lambda_2$ into body tissue 1 at a first temperature $T_1$, d) recording secondary light 7 that is back scattered by the body tissue and storing the intensity of the secondary light in a second memory 19 according to its wavelength as a second Raman spectral signal for the second wavelength $\lambda_2$ and the first temperature $T_1$, e) comparing the first Raman spectral signal in the first memory 12 with the second Raman spectral signal in the second memory 19 and generating a compare signal for which spectral structures caused by the body tissue are substantially eliminated, f) determining an intensity of the compare signal at at least one sample wavelength $\lambda_3$ g) repeating steps a) to f) at a second temperature $T_2$ and generating a second compare signal at at least one sample wavelength $\lambda_3$ for which the intensity of the secondary light for the first and second wavelength $\lambda_1$, $\lambda_2$ are stored in a third 26 and fourth memory 28, respectively, and a second compare signal is generated, h) comparing the first and the second compare signal and, depending on the result of this comparison, generating an identification signal at at least one sample wavelength $\lambda_3$, which indicates whether a temperature dependent signal change is available at at least one sample wavelength $\lambda_3$. The procedure of this kind represents a very sensitive, multiply different method for the detection of substances. In particular, by changing both parameters. the remaining undulation (shift of the background structures in the difference spectrum) in the first two compare spectra can be eliminated, so that the baseline in the difference spectrum, for this method, comprises even less structures compared to the "simple" comparison. In this way a higher accuracy and reproducibility can be achieved for the determination of the concentration of the sought after substance. The temperature changes between $T_1$ and $T_2$ are preferably synchronised with the systole/diastole cycle of the blood circulation.

In case of the procedure using the device according to FIG. 3 the primary light 3 of the first and/or second wavelength is irradiated preferably with a preset irradiation frequency and the first and the second Raman spectral signal is recorded at the irradiation frequency by a lock-in amplifier 30. For that the irradiation frequency lies preferably in the region of some hertz to kilohertz.

All procedures are carried out preferably for secondary light 7 in the Stokes region and/or anti-Stokes region of the Raman spectrum in order to enhance the detection and measurement sensitivity further. This means that the recorded wavelength region for secondary light is shifted towards shorter wavelengths compared to the primary wavelengths $\lambda_1$, $\lambda_2$ (anti-Stokes) and to longer wavelength regions (Stokes), respectively.

The wavelengths $\lambda_1$, $\lambda_2$ of primary light 3 lie in a region in which the body tissue is essentially transparent, viz. between 750 nm and 850 nm, and the modulus of the difference of the wavelengths $\lambda_1$, $\lambda_2$ of primary light 3 and the sample wavelength $\lambda_3$ is for instance preferably less than 250 meV (2000 cm$^{-1}$) for measurement of glucose, but greater than 2.5 meV (20 cm$^{-1}$).

Apart from this essentially at the same time as primary light 3 an excitation light wavelength $\lambda_{exc}$ can be irradiated into the body tissue 1, which is absorbed by the substance, so that excitation of vibrational bands arises in the sought after molecule. This can be observed in the measurement signal. The excitation light wavelength $\lambda_{exc}$ lies between 1.2 $\mu$m and 3 $\mu$m for glucose.

A calibration of the concentration of the substance to be detected in body fluids or in body tissue requires a constant reference signal independent of the concentration of the substance to be detected. This is performed by the comparison of a measurement signal assigned to the substance to be detected with a known constant measurement signal from the same scattering volume in body tissue 1. Suitable for this is the more or less constant background signal (slope in FIGS. 4A, 4B; 5A, 5B), as well as the Raman signal originating from water or another substance whose concentration is known or constant. The intensity comparison of the signal from the substance with the reference signal results in the calibration of the substance concentration. Alternatively, from the reference signal, the scattering volume can be determined from which the secondary light is collected and from the scattering volume the signal for the substance to be detected can be calibrated and therefore its concentration determined. In other words for the calibration of the determination of the concentration of the sought after substance the intensity of the first compared signal at at least one sample wavelength $\lambda_3$ is compared with the intensity of the first and/or second Raman spectral signal at a different sample wavelength $\lambda_4$. For instance, the calibration of the concentration determination of a sought after substance can be carried out as clinical calibration (at a different place and at a different time as the actual measurement).

In case of a further improved embodiment of the procedure according to the invention the identification of the glucose signal and the determination of the glucose concentration is carried out by employing multivariate statistical mathematical methods for comparison and for analysis of the measured Raman spectral signals which are known per se. In this the multivariate statistical mathematical procedures are implemented in a computer system that is connected to the device according to the invention. In case of application at a patient an as large as possible number of Raman spectra is measured at different points in time and stored in the memory unit. It is known as well in the art that these measurements then serve to establish a calibration model via a multivariate statistical regression, (for instance a principal component regression). For a new measurement the glucose concentration, then is determined with a certain standard deviation using the regression coefficients obtained from the calibration model. The more data readings are available for the evaluation the smaller becomes the standard, deviation for the glucose concentration. The means is in a position to arrive at an improvement of the accuracy of the determination of the glucose concentration by 'learning', that is by data accumulation and improvement of the calibration model obtained from the multivariate statistical analysis.

In summary: The invention concerns a procedure and means for the non-invasive detection and, respectively, determination of the concentration of substances in body fluids by Raman spectroscopy. For achieving the goal of a non-invasive in-vivo detection of substances in body fluids with very good reproducible accuracy of analysis for small measurement periods acceptable for the patient, a method and a device is provided to carry out a Raman spectroscopy of a body fluid in a body tissue 1 for which at least two Raman spectra are recorded under different physical conditions and compared with each other. The compare result constitutes the detection of the sought after substance and a measure of its concentration, respectively.

Based on the principal of the invention further embodiments going beyond those described above are conceivable. For example, it is obviously possible to use a single laser means as first and second light source 2 and 13, for instance, a laser diode which is tuneable by changing an electric parameter with high repetition rate, so that a first wavelength $\lambda_1$ and a second wavelength $\lambda_2$ (not too far from the first) allows to be produced by the same light source.

Furthermore the beam paths 3 and 7 can be particularly well adapted to the conditions and environment of the examination if the light is coupled into waveguides or optical fibres and if light is collected by these, respectively.

Apart from that, evidently the term 'heating means' is understood also as a means for alternating heating and cooling in the above description. For a means that is useful as well for heating as for cooling the useful temperature difference between $T_1$ and $T_2$ can be increased without damaging the body tissue so that a better signal to noise ratio results.

The spectra in the first, second, third and fourth memory are recorded over a preset wavelength range, respectively. Improvement of the measurement statistics can be carried out by several measurement sequences, among others with lock-in amplification, for all procedures and embodiments.

While specific embodiments of the present invention have been shown and described, further modifications and improvements will occur to those skilled in the art. It is understood that the invention is not limited to the particular forms shown and the appending claims are intended to cover all modifications which do not depart from the scope of this invention as defined in the appending claims.

What is claimed is:

1. A method for the non-invasive determination of a concentration of a substance in a body fluid in a body tissue by Raman spectroscopy comprising the steps:
   a) irradiating monochromatic primary light of a first wavelength into the body tissue,
   b) recording secondary light that is back scattered by the body tissue and storing the intensity of the secondary light in a first memory according to its wavelength as a first Raman spectral signal for the first primary wavelength,
   c) irradiating monochromatic primary light of a second wavelength into the body tissue,
   d) recording secondary light that is back scattered by the body tissue and storing the intensity of the secondary light in a second memory according to its wavelength as a second Raman spectral signal for the second primary wavelength,
   e) comparing the first Raman spectral signal in the first memory with the second Raman spectral signal in the second memory and generating a compare signal in which spectral structures caused by the body tissue are substantially eliminated,
   f) determining an intensity of the compare signal at at least one sample wavelength for which the intensity corresponds to the concentration of the substance in the body fluid,
   wherein the primary light of the first and second wavelength is irradiated with a preset irradiation frequency and each Raman spectral signal is recorded with said irradiation frequency.

2. The method according to claim 1, wherein the secondary light is recorded and the intensity of the compare signal is determined in the Stokes and anti-Stokes region of the Raman spectrum.

3. The method according to claim 2, wherein an excitation light is irradiated into the body tissue which is absorbed by the substance.

4. The method according to claim 3, wherein the excitation light is pulsed with a pulse length in the picosecond region.

5. The method according to claim 4, wherein the primary light is pulsed with a pulse length in the picosecond region.

6. A method for non-invasive determination of a concentration of a substance in body tissue by Raman spectroscopy comprising the steps:
   a) irradiating monochromatic primary light of a first wavelength into the body tissue at a first temperature of the body tissue,
   b) recording secondary light that is back scattered by the body tissue and storing the intensity of the secondary light in a first memory according to its wavelength as a first Raman spectral signal for the first wavelength and for the first temperature,
   c) irradiating monochromatic primary light of a second wavelength into the body tissue at a first temperature of the body tissue,
   d) recording secondary light that is back scattered by the body tissue and storing the intensity of the secondary light in a second memory according to its wavelength as a second Raman spectral signal for the second wavelength and the first temperature,
   e) comparing the first Raman spectral signal in the first memory with the second Raman spectral signal in the second memory and generating a compare signal for which spectral structures caused by the body tissue are substantially eliminated,
   f) determining an intensity of the compare signal at at least one sample wavelength,
   g) repeating steps a) to f) for a second temperature and generating a second compare signal at at least one sample wavelength for which the intensity of the secondary light for the first and second wavelength is stored in a third and a fourth memory, respectively, and a second compare signal is generated,
   h) comparing the first and the second compare signal and, depending on the result of this comparison, generating an identification signal at at least one sample wavelength.

7. The method according to claim 6, wherein the primary light is irradiated and each Raman spectral signal is recorded with a preset irradiation frequency.

8. The method according to claim 7, wherein the body tissue temperature is adjusted with a preset temperature variation frequency.

9. The method according to claim 6, wherein the body tissue temperature is adjusted with a preset temperature variation frequency.

10. The method according to claim 6, wherein the secondary light is recorded and the intensity of the compare signal is determined in the Stokes and anti-Stokes region of the Raman spectrum.

11. The method according to claim 6, wherein the secondary light is recorded and the intensity of the compare signal is determined in the Stokes and anti-Stokes region of the Raman spectrum.

12. A device for the non-invasive determination of a concentration of a substance in a body fluid in a body tissue by Raman spectroscopy comprising:
   a) a first light source for irradiating monochromatic primary light of a first wavelength into the body tissue,
   b) a photo detector means for recording secondary light that is backscattered from the body tissue,
   c) a first memory for storing the intensity of the secondary light according to its wavelength as a first Raman spectral signal for the first wavelength,
   d) a second light source for irradiating monochromatic primary light of a second wavelength into the body tissue,
   e) a second memory for storing the intensity of the secondary light, according to its wavelength as a second Raman spectral signal for the second wavelength,
   f) a comparator means for comparing the first Raman spectral signal in the first memory with the second Raman spectral signal in the second memory and for generating a compare signal for which spectral structures caused by the body tissue are substantially eliminated,
   g) a discriminator unit for determining an intensity of the compare signal at at least one sample wavelength for which the intensity corresponds to the concentration of the substance in the body fluid, the first and second primary light source, the photo detector means and the first and the second memory being pulsed with a preset irradiation frequency.

13. The device according to claim 12, wherein a third light source is provided for irradiating excitation light into the body tissue, which is absorbed by the substance.

14. The device according to claim 13, wherein the third light source is pulsed with a pulse length in the picosecond region.

15. The device according to claim 14, wherein the first and second light source is pulsed with a pulse length in the picosecond region.

16. A device for the non-invasive determination of a concentration of a substance in a body fluid in a body tissue by Raman spectroscopy comprising:
   a) a first light source for irradiating monochromatic primary light of a first wavelength into the body tissue,
   b) a second light source for irradiating monochromatic primary light of a second wavelength into the body tissue,
   c) a heating means for adjusting a first temperature and a second temperature in the body tissue,
   d) a photo detector means for recording secondary light that is backscattered from the body tissue,
   e) a first memory for storing the intensity of the secondary light according to its wavelength as a first Raman spectral signal for the first wavelength and for the first temperature, a second memory for storing the intensity of the secondary light according to its wavelength as a second Raman spectral signal for the second wavelength and for the first temperature, a third memory for storing the intensity of the secondary light according to its wavelength as a third Raman spectral signal for the first wavelength and for the second temperature and a fourth memory for storing the intensity of the secondary light according to its wavelength as a fourth Raman spectral signal for the second wavelength and for the second temperature,
   f) a first comparator means for comparing the first Raman spectral signal in the first memory with the second Raman spectral signal in the second memory and for generating a compare signal for which spectral structures caused by the body tissue are substantially eliminated,
   g) a second comparator means for comparing the third Raman spectral signal in the third memory with the fourth Raman spectral signal in the fourth memory and for generating a compare signal for which spectral structures caused by the body tissue are substantially eliminated,
   h) a third comparator means for comparing the first compare signal with the second compare signal for generating a third compare signal depending on the result of this comparison,
   i) a discriminator unit for determining an intensity of the third compare signal at at least one sample wavelength,
   j) an output unit for the output of an identification signal according to the intensity at at least one sample wavelength for which the intensity corresponds to the concentration of the substance in the body fluid.

17. The device according to claim 16, wherein the first and second light source, the photo-detector means and each memory is pulsed with a preset irradiation frequency.

18. The device according to claim 17, wherein the heating means is pulsed with a preset temperature variation frequency.

19. The device according to claim 16, wherein the heating means is pulsed with a preset temperature variation frequency.

20. A method for the non-invasive determination of a concentration of a substance in a body fluid in a body tissue by Raman spectroscopy comprising the steps:
   a) irradiating monochromatic primary light of a first wavelength into the body tissue at a first parameter value,
   b) recording secondary light that is back scattered by the body tissue and storing the intensity of the secondary light in a first memory according to its wavelength as a first Raman spectral signal for the first primary wavelength and for the first parameter value,
   c) repeating steps a) and b) for other primary wavelengths and other parameter values for which the intensity of the secondary light is stored in a further memory for each further primary wavelength and for each further parameter value,
   d) multivariate statistical comparison of the Raman signals for determining at least one sample wavelength for which the intensity changes analogously to the parameter values, and
   e) determining and outputting the intensity at at least one sample wavelength in several Raman spectral signals according to the parameter values.

21. The method according to claim 20, wherein the parameter is the blood sugar level.

* * * * *